US011969548B2

(12) United States Patent
Hieronymus et al.

(10) Patent No.: US 11,969,548 B2
(45) Date of Patent: Apr. 30, 2024

(54) NASAL APPLICATOR

(71) Applicant: 5med GmbH, Bad Abbach (DE)

(72) Inventors: Jens Hieronymus, Darmstadt (DE); Klaus Sinner, Munich (DE); Stefan Nardi-Hiebl, London (GB)

(73) Assignee: 5MED GMBH, Bad Abbach (DE)

( * ) Notice: Subject to any disclaimer, the term of this patent is extended or adjusted under 35 U.S.C. 154(b) by 719 days.

(21) Appl. No.: 17/073,029

(22) Filed: Oct. 16, 2020

(65) Prior Publication Data

US 2021/0030982 A1 Feb. 4, 2021

Related U.S. Application Data

(63) Continuation of application No. 15/741,837, filed as application No. PCT/EP2016/001083 on Jun. 24, 2016, now Pat. No. 10,835,695.

(30) Foreign Application Priority Data

Jul. 6, 2015 (DE) ..................... 20 2015 004 852.8

(51) Int. Cl.
*A61M 15/08* (2006.01)
*A61M 15/00* (2006.01)
*A61K 9/00* (2006.01)

(52) U.S. Cl.
CPC ........ *A61M 15/08* (2013.01); *A61M 15/0028* (2013.01); *A61K 9/0043* (2013.01); *A61M 15/0068* (2014.02)

(58) Field of Classification Search
None
See application file for complete search history.

(56) References Cited

U.S. PATENT DOCUMENTS 6,981,499 B2   1/2006 Anderson et al.
9,033,939 B2   5/2015 Eberhart et al.
(Continued)

FOREIGN PATENT DOCUMENTS

DE   60212837 T2   6/2007
DE   60033176 T2   10/2007
(Continued)

OTHER PUBLICATIONS

ISA European Patent Office, International Search Report Issued in Application No. PCT/EP2016/001083, dated Sep. 29, 2016, WIPO, 4 pages.

*Primary Examiner* — Bradley H Philips
*Assistant Examiner* — Savannah L Gabriel
(74) *Attorney, Agent, or Firm* — McCoy Russell LLP

(57) ABSTRACT

A nasal applicator for nasally applying medicinal active ingredients, comprising a dispensing pin which is introduced into a nostril, a active ingredient store arranged in an applicator housing, and a dispensing metering device. A transmitting device is designed so as to be engageable and disengageable between an actuation button and the dispensing metering device such that when the transmitting device is disengaged, the actuation button is moved in the open passage without a transmission to the dispensing metering device. A movement sensor is provided for detecting movements of the operating button, and a coupling switch is provided for engaging the transmitting device depending on a signal of the movement sensor. To generate a consistent spray pattern, the dispensing metering device comprises a pretensioning mechanism which can be tensioned or released to actuate a metering conveyor with a defined pretensioning force, wherein the engaged transmitting device can tension or release the pretensioning mechanism.

4 Claims, 7 Drawing Sheets

(56) References Cited

U.S. PATENT DOCUMENTS

| | | | |
|---|---|---|---|
| 2002/0000225 A1* | 1/2002 | Schuler | A61M 15/008 128/200.14 |
| 2005/0022806 A1 | 2/2005 | Beaumont et al. | |
| 2005/0098583 A1 | 5/2005 | Mbonyumuhire | |
| 2009/0120962 A1* | 5/2009 | Malorni | A61M 15/009 222/638 |
| 2010/0308082 A1* | 12/2010 | Lamble | B05B 11/1074 222/162 |
| 2011/0088690 A1 | 4/2011 | Djupesland et al. | |
| 2011/0265788 A1* | 11/2011 | Wu | A61M 15/009 222/23 |
| 2013/0239957 A1* | 9/2013 | Pinfold | A61M 15/0091 128/200.23 |

FOREIGN PATENT DOCUMENTS

| | | |
|---|---|---|
| DE | 102013012292 B3 | 1/2014 |
| DE | 202012008892 U1 | 2/2014 |
| EP | 0689848 A1 | 1/1996 |
| EP | 1293224 A2 | 3/2003 |
| FR | 2721521 A1 | 12/1995 |
| GB | 2389316 A | 12/2003 |
| GB | 2408214 A | 5/2005 |
| WO | 2007081947 A2 | 7/2007 |
| WO | 2016100564 A1 | 6/2016 |

\* cited by examiner

NASAL APPLICATOR

CROSS-REFERENCE TO RELATED APPLICATIONS

The present application is a continuation of U.S. National Phase application Ser. No. 15/741,837 entitled "NASAL APPLICATOR", filed on Jan. 4, 2017. U.S. National Phase application Ser. No. 15/741,837 claims priority to International Patent Application Serial No. PCT/EP2016/001083, entitled "NASAL APPLICATOR," filed on Jun. 24, 2016. International Patent Application Serial No. PCT/EP2016/001083 claims priority to German Patent Application No. 20 2015 004 852.8, filed on Jul. 6, 2015. The entire contents of the above-listed applications are hereby incorporated by reference for all purposes.

TECHNICAL FIELD

The present invention relates to a nasal applicator for a nasal administration of medicinal active ingredients, in particular analgesics, comprising a dispensing pin which can be introduced into a nostril, a connectable active ingredient store arranged in an applicator housing, and a dispensing meter for a metered dispensing of the active ingredient from the active ingredient store via the dispensing pin.

BACKGROUND AND SUMMARY

In analgesic therapy, strong analgesics or opioids sometimes have to be administered, with it being advantageous to achieve a fast onset of action to administer these analgesics via the nasal mucous membrane. Nasal applicators provided for this purpose are known in various forms and can be operated in a simple manner by the patients themselves. A dispensing pin of the nasal applicator is introduced into a nostril and is then actuated to dispense a predefined dose of the analgesic, for example in an atomized form of an aerosol. A dispensing metering mechanism provided in the interior of the nasal applicator can, for example, comprise a motor-powered pump, but is sometimes also a manually actuated discharge mechanism that can, for example, work by compressing the applicator housing or by pressing a discharge piston.

It this respect, it has already been thought of to use nasal spray cartridges that are conventional per se and that have an integrated discharge or pumping apparatus that can be actuated by moving the dispensing pin toward the cartridge container in that, for example, two holding fins of the dispensing pin are held by two fingers and the cartridge is pressed onto the dispensing pin by the thumb. To prevent an improper use, in particular an unauthorized use or an overdose use of such commercial nasal spray cartridges, these nasal spray cartridges can be inserted into an applicator housing to selectively block or release the dispensing of the active ingredient from the nasal spray cartridge and optionally also to be able to facilitate the operation, which can in particular be helpful for infirm or enfeebled patients. The active ingredient container of the nasal spray cartridge can here be displaceably received in the applicator housing, while the dispensing pin can be held firmly or can contact an abutment so that the discharge device of the nasal spray cartridge can be actuated by a displacement of the active ingredient container relative to the applicator housing.

An actuation button can be arranged movable by hand at the applicator housing for this purpose, for example in the form of an actuating lever or an actuating tap that can project at the peripheral side at the applicator housing and that can be pressed in the radial direction so that an actuation can be brought about in a similar manner to a natural gripping movement by compressing by the hand or first gripping the applicator housing. In general, such an actuation button can, however, also be designed in the manner of a slider or of a push button that can be linearly pressed or in the manner of a rocker switch or of a rotary switch. The actuation movement of said actuation button can here be transmitted to the dispensing meter by a transmitter that then provides the active ingredient discharge.

Nasal applicator of the initially named kind are known, for example, from the documents US 2005/0098583, FR 2 721 521 or GB 2 408 214, with the last-named GB 2 408 214 providing a blocking of the active ingredient dispensing on an improper insertion of the applicator. FR 2 721 521 shows a nasal applicator for nasal powder application.

Whereas, on the one hand, self-administration is sensible and desired with analgesics in order only to take the analgesic when it is actually needed, the patient self-administering the analgesic, on the other hand, has to be protected from an unintentional overdose, in particular when it is a strong-action opioid analgesic.

Document DE 10 2013 012292 proposes for this purpose providing a dose detection device at the nasal applicator by means of which the dispensed amount of active ingredient is detected. Once a respective permitted maximum dose has been reached, the dispensing meter is blocked so that no further strokes or doses can be dispensed. The maximum dose can here be programmed for an individual patient, for example in an RFID chip fastenable to the patient's wrist from which the control apparatus of the nasal applicator reads the permitted maximum dose and correspondingly releases or blocks the dispensing meter.

There is, however, a problem with such nasal applicators operable autonomously by the patient in that the valves and discharge pumps controllable by an electronic control apparatus require a relatively large amount of current and thus larger storage batteries or cells that make the nasal applicator heavy and awkward to operate. There is the additional fact in this respect that the applicator per se should be permanently ready for use without first having to be switched on and booted to enable a self-administration of the active ingredient for the patient as required fast and at all times. A corresponding standby circuit, however, further increases said power requirement.

A mechanical actuation of the metering conveyor that dispenses with electric pumps and valve devices actuated by external energy would be suitable per se for avoiding or alleviating this problem. Such mechanical actuation apparatus that actuate the dispensing meter by muscular strength are, however, problematic as regards the exact dosage and an unchanging, reproducible performance of the metering strokes since the dispensed dose can fluctuate in dependence on whether the actuation is powerful or less powerful, fast or slow or whether the actuation button is moved further or less far.

Even if the actuation button is pulled or pushed through completely so that the complete adjustment path is produced per se with the total discharge volume associated therewith, impairments or deviations in the spray pattern can occur on too slow an actuation and where applicable also on too fast an actuation or on in insufficiently forceful actuation. Such deviations in the spray pattern can result, for example, in that on too slow an actuation, the droplets remain relatively large or the active ingredient is not atomized sufficiently finely so that the active ingredient absorption by the body is impaired since it depends greatly on the droplet size or particle size. In this respect, too small or too fine an atomization can in principle also be an obstacle since then the active ingredient is no longer deposited on the nasal wall, but is rather directly inhaled, which can be desirable or undesirable depending on the active ingredient. On the other hand, deviations in the spray pattern can also be caused by the discharge speed that can vary in dependence on the actuation power and actuation speed, which can then, for example, be reflected in a narrower spray cone that carries further or, conversely in a wider spray cone that carries less and can accordingly act differently on different regions of the interior of the nose, which can in turn have effects on the active ingredient absorption. Larger deviations in the actuation speeds and in the actuation forces can in particular occur in older or more infirm patients which result in unwanted deviations in the spray pattern in the named manner.

On the other hand, it is also not that simple with such mechanical actuation mechanisms to design a block of the actuator in a manner sufficiently secure against manipulation without forming the mechanical actuation train or drive train in a solid and lumpy manner. To prevent the actuation button from being pressed down once more by force against a block—for example after reaching the permitted daily dosage—the ratchet or a similar blocking element would have to be formed sufficiently solidly and would also have to be protected from manipulation from outside, for example by a screwdriver or a needle, by a solid housing design. However, this in turn stands in the way of a light-weight unit design and impairs an easy handling.

Starting from this, it is the underlying object of the present invention to provide an improved nasal applicator of the named type which avoids disadvantages of the prior art and further develops the latter in an advantageous manner. A precise and easy to effect self-metering of very powerful analgesics should in particular be made possible without requiring an awkward, heavy metering conveyor that consumes a high storage battery power for this purpose.

The named object is achieved in accordance with the invention by a nasal applicator for nasal administration of medicinal active ingredients, comprising an active ingredient store arranged in an applicator housing; a dispensing pin which is introduced into a nostril; and a dispensing meter for a metered dispensing of the active ingredient from an active ingredient container via the dispensing pin, wherein an actuating button movable by hand is provided at the applicator housing for actuating the dispensing meter whose actuation adjustment path is transmitted to the dispensing meter by a transmitter, wherein the transmitter is configured couplable and decouplable so that, with a decoupled transmitter, the actuation button is movable in free travel without transmission to the dispensing meter; wherein a motion sensor is provided for detecting movements of the actuating button and a coupling switch is provided for coupling the transmitter in dependence on a signal of the motion sensor. Embodiments of the invention are the subject of the dependent claims.

It is therefore proposed to give the actuating button a free-wheel or free travel with respect to the dispensing meter and only to establish an active connection or drive connection between the actuating button and the dispensing meter in exceptional cases—namely when an authorized metering stroke is to be carried out. Due to the active connection being cut in the normal or starting condition, the actuation button can be depressed without activity without this resulting in the actuation of the dispensing meter so that solid blocking elements for blocking the actuation button can be dispensed with while, on the other hand, with an established active connection, a simply manual operation can take place that does not require any heavy cells or storage batteries. In accordance with the invention, the transmitter is formed as couplable and decouplable between the actuating button and the dispensing meter so that, with a decoupled transmitter, the actuating button is movable in free travel without transmission to the dispensing meter, with a motion sensor for detecting movements of the actuation button and a coupling switch for coupling the transmitter in dependence on a signal of the motion sensor being provided. The actuating button has a dual function through the motion sensor since it can be used, on the one hand, to activate or wake up the system and, on the other hand, to actuate the dispensing meter. If the actuation button is first actuated from the starting position, the motion sensor detects it and reports it to the coupling switch that can then couple the transmitter and can thus switch the actuation mechanism live.

In an advantageous further development of the invention, said coupling switch can here also take account of other signals or operating parameters and not only couple the transmitter on a detected movement of the movement button, but also so-to-say only utilize the signal of the motion sensor to query further operating parameters of the system with reference to which a decision is then made whether the transmitter is actually coupled or not. Said coupling switch can in particular be released by a control apparatus in dependence on an already administered dosage and/or in dependence on a permitted maximum dosage and/or in dependence on the presence of an identification code individual to the patient and/or in dependence on the presence of a release code and/or in dependence on a time switching code and/or in dependence on the presence of an RFID signal. In particular when an actuation of the actuating button has been reported by the motion sensor, said coupling switch or said control apparatus can query whether an RFID signal is present or can be queried that contains a predefined release code. If this is the case, the coupling switch can then couple the transmitter. In a similar manner, a query can be made after the report of an actuation button movement whether and/or at what level an active ingredient dose was already administered in a past time window and/or whether a permitted maximum dose or maximum daily dose has already been reached and/or whether an authorized operator is in the vicinity of the device—for example by transmitting an identification code individual to the patient. A user can, for example, for this purpose use an RFID arm band or an RFID element that can be worn at or fastened to a different part of the body to decide via a wireless communication link with reference to the data transmitted by the RFID element whether the transmitter should be coupled. Alternatively or additionally, a fingerprint sensor can also be provided to identify the operator.

Alternatively or additionally to such an electronic signal code, a mechanical fastening block that blocks said actuating button and first has to be released to enable a movement of the actuating button can also be provided for protection from unintended or imprudent triggering. Such a child-proof lock or multi-hand or multi-finger actuation can, for example, be implemented by one or more additional unblocking buttons that can, for example, work in the manner of a latch transversely to the actuation button. In a further development of the invention, two blocking jaws can, for example, be provided at the applicator housing that can be depressible or movably supported transversely to the actuation plane of the actuation button so that they release the operating button by depression and block the actuation button in the non-depressed position.

To avoid an unnecessary switching on of the nasal applicator or an unnecessary operation of the control apparatus, said coupling switch and/or said motion sensor can have a response threshold that leaves small deflections of the actuation button from its starting position out of consideration. The coupling switch or the control apparatus associated therewith therefore only reacts when the actuation button has covered a certain path distance on whose exceeding it can be reasonably assumed that it is a deliberate actuation of the actuation button. Said response threshold can, for example, amount to 20% to 50% of the maximum adjustment path; that is, can only provide a reaction of the coupling switch when the actuation button is moved, for example, by a quarter of its provided path. Said response threshold can, however, also be smaller or larger depending on the adjustment path and on the design of the actuation button.

To reliably avoid operator errors, a coupling of the transmitter can also only be carried out on a multiple actuation of the actuation button or the coupling switch can convert an actuation of the actuation button into a coupling movement in dependence on the path distance and in dependence on the cycle. The coupling switch can in particular be configured as working in dependence on the motion sensor such that the transmitter is only coupled when the actuation button is moved back into the starting position after a first button stroke, that can take place in free travel, so that the adjustment movement of the actuating button is transmitted to the dispensing meter in a second or further button stroke. An actuation of the dispensing meter can hereby be initialized in the manner of a double click or multiple click of a computer mouse—on the presence of possibly required further release signals such as the previously named release code. A first depression or optionally also a multiple depression, for example a double or triple depression, in the free travel effects a waking or activating of the actuation mechanism and causes the coupling switch to couple the transmitter and to establish an active connection between the actuation button and the dispensing meter while a following or further actuation stroke of the actuation button is converted into an actuation of the dispensing meter. The coupling switch can therefore be configured such that it only activates the transmitter when a predetermined number of actuation button actuations has been detected in the free travel, with this only needing to be a free-travel blank actuation in a simple case in order then to convert the actuation setting movement into a metering stroke immediately on the second actuation button actuation.

To prevent the dispensing meter from being operated multiple times in an unintentional or unauthorized manner, for example by a fast multiple actuation of the actuation button, after establishing the active connection between the actuation button and the dispensing meter, said coupling switch can have an interval timer for a coupling of the transmitter only limited in time so that the transmitter decouples again after the elapse of a predefined time interval that can also be very short.

Alternatively or additionally, the coupling switch can also have a metering stroke circuit for coupling the transmitter only for a single metering stroke. Such a metering stroke circuit can generally be implemented in various ways, for example by detecting a return movement of the actuation button by said motion sensor, in particular such that when the actuation button travels back into its starting position again after a depression, the coupling switch is deactivated or the transmitter is decoupled again.

Alternatively or additionally, the transmitter can also be preloaded into its decoupled position, for example by means of a spring apparatus or a preload apparatus or also only by gravity, with the transmitter only being held in its coupling position with force transmission or with frictional engagement or with shape matching in that the actuation button is pressed or pulled. If the engagement pressure between the transmitter and the actuation button drops, for example because the actuation button is released or moved back, the preload force can release the engagement between the transmitter and the actuation button so that the transmitter falls back into its decoupled position.

Said transmitter can be part of a multi-member and/or multi-piece and/or multi-jointed transmitter mechanism and/or transmitter train that, in a further development of the invention, can be configured as purely mechanical and/or can achieve an actuation of the active ingredient conveyor or dispensing meter by muscular force. It would, however, generally likewise be possible to provide adjustment actuators actuable by external energy in an assisting manner or also in a manner completely effecting the discharge so that the adjustment movement of the actuating button essentially only serves the putting into operation of such an adjustment actuator actuated by external energy and/or the triggering of an adjustment mechanism or drive mechanism previously loaded by motor power or by external energy. In order, however, not to require large cells, an actuation of the dispensing meter substantially completely by muscular force can be provided.

The dispensing meter or its active ingredient conveyor can here generally be actuated or operated directly by the transmitter from the actuation button. If, for example, the active ingredient container of an active ingredient cartridge or nasal spray cartridge is displaceably received in the applicator housing in the initially named manner, the transmitter can convert the adjustment movement of the actuation button and convert it directly into an adjustment movement or displacement movement of the active ingredient container to thereby actuate the active ingredient cartridge. A simple design of the active train or drive train between the actuation button and the metering conveyor can hereby be achieved.

An optionally multi-piece or multi-member lever mechanism can nevertheless be provided here to enable a simple actuation with little force, said lever mechanism converting the actuation button movement into the desired cartridge movement, with said transmitter being able to be part of said lever mechanism.

Alternatively to such a direct actuation, however, an only secondary or indirect actuation of the metering conveyor or dispensing meter by the actuation button can also be provided in accordance with a further aspect of the present invention. In this respect, the dispensing meter can have a loadable and triggerable preload mechanism for actuating the metering conveyor with a defined preload force, with the preload mechanism being configured as loadable by the transmitter against a retainer and with the retainer being configured as releasable by the transmitter so that the preload mechanism is both loadable and releasable by the transmitter. Such an indirect actuation of the dispensing meter by muscular force whose actuation of the actuation button is converted into the loading of the preload mechanism can be provided in addition to the previously explained coupling and decoupling capability of the transmitter, but can also be advantageously independently thereof to enable a precise, exact reproducible metering of the active ingredient. A defined spray pattern that has said droplet size or that atomizes the active ingredient with the desired fineness and that includes an always unchanging spray cone can in particular be generated by such a preload mechanism that is triggered via the transmitter by the actuation button. Said loaded preload mechanism generates a defined adjustment force and adjustment speed that is reflected in the desired spray pattern independently of how fast or powerfully the actuator is depressed. Since the metering conveyor does not directly depend on the speed or the power of the actuation force, but rather on the preload force of the preload mechanism, the exactly desired dose amount can be dispensed with each stroke and the desired spray pattern can be achieved. At the same time, an energy-saving design of the applicator can be achieved since adjustment actuators and pumps and the like actuated by external energy can be dispensed with.

The combination of such a preload mechanism with an actuator that triggers the preload mechanism can also already generate the desired, always non-changing or reproducible spray pattern when the actuator is only provided for triggering the preload mechanism and the preload mechanism can be loaded via a load actuator actuable by external energy, for example in the form of a cell-operated motor that can load an adjustment spring via a spindle, for example. The actuator and/or the transmitter connected thereto can optionally start the load actuator actuable by external energy or can put it into operation, for example in that the actuator motor that then loads the preload mechanism is started by a first depression and a second depression triggers the loaded preload mechanism. In other words, the preload mechanism is not necessarily loaded by muscular force. Nevertheless, a light-weight design of particularly small dimensions can be achieved without any dependence on the service life of cells when said preload mechanism is loadable by the actuation button and by the transmitter connected thereto and thus by muscular force.

In a further development of the invention, an interaction of the retainer and the loader of the preload mechanism with different sections of the adjustment path of the transmitter or a time-graduated interaction between the transmitter and the retainer and between the transmitter and the loader can be provided, in particular such that the transmitter first only actuates the loader and only releases the retainer when the preload mechanism is completely loaded.

The retainer can in particular be associated with a different section of the adjustment path of the transmitter than said loader. The retainer is advantageously arranged relative to the adjustment path of the transmitter such that the retainer only moves into engagement with the transmitter in an end section of the adjustment path of the transmitter and is only triggered when the preload mechanism is completely loaded.

The transmitter is hereby given a dual function, namely a loading, on the one hand, and a triggering, on the other hand. The loading and the triggering of the preload mechanism can advantageously be carried out with only one actuation, for example a simple depressing of the actuating button. The applicator operator does not have to actuate different buttons or depress the actuation button a multiple of times.

Said preload mechanism can advantageously have a lifting apparatus, for example in the form of a toggle lever, that converts the movement of the transmitter into a load movement of a spring device at a corresponding lever ratio. Said spring device can here advantageously be a mechanical spring, for example in the form of a spiral spring, or can also comprise a gas or fluid compression spring device. A simple handling with small forces can also be achieved by infirm patients by a use of such a lever mechanism.

If the dispensed active ingredient amount is detected in the previously named manner by means of a metering detection device, the nasal applicator can ensure that the maximum dose compatible for a patient is observed or is not exceeded, for example in that the control apparatus blocks the coupling switch or holds the transmitter out of engagement when the permitted maximum dose is reached.

In this respect, the nasal applicator can be individually configured with respect to the dispensable maximum active ingredient amount, with a maximum quantity being able to be predefined, on the one hand, per time, for example in the form of micrograms/hour, and/or, on the other hand, also absolute maximum amounts, for example with active ingredients that cannot be easily degraded, on whose reaching the blocking apparatus is respectively actuated to block the dispensing meter so that the dispensing meter can only dispense the respective individually predefined maximum active ingredient amount. Said permitted maximum active ingredient amounts can be variably predefined by inputting corresponding control data into said patient data store. In a further development of the invention, the application amounts or maximum application amounts that are dispensed by the dispensing meter can be controlled, for example in dependence on the patient's weight or his/her opioid habits.

The configuration individual to the patient can generally take place in different manners here. The nasal applicator or its control apparatus and/or its patient data store can, for example, be connected via a data transfer interface to a higher order external processor from where the required control data for the respective patient or user can be imported.

Alternatively or additionally to the configurability via an external data transfer interface, the nasal applicator itself can also be provided with suitable input means that enables the input of the control data individual to the patient to the control apparatus or to its patient data store, for example in the form of a keyboard and/or of a touchscreen, either directly at the housing or in connectable form, for example in the manner of an external PC keyboard.

BRIEF DESCRIPTION OF THE FIGURES

The present invention will be explained in more detail in the following with reference to a preferred embodiment and to associated drawings.

Figure 1:
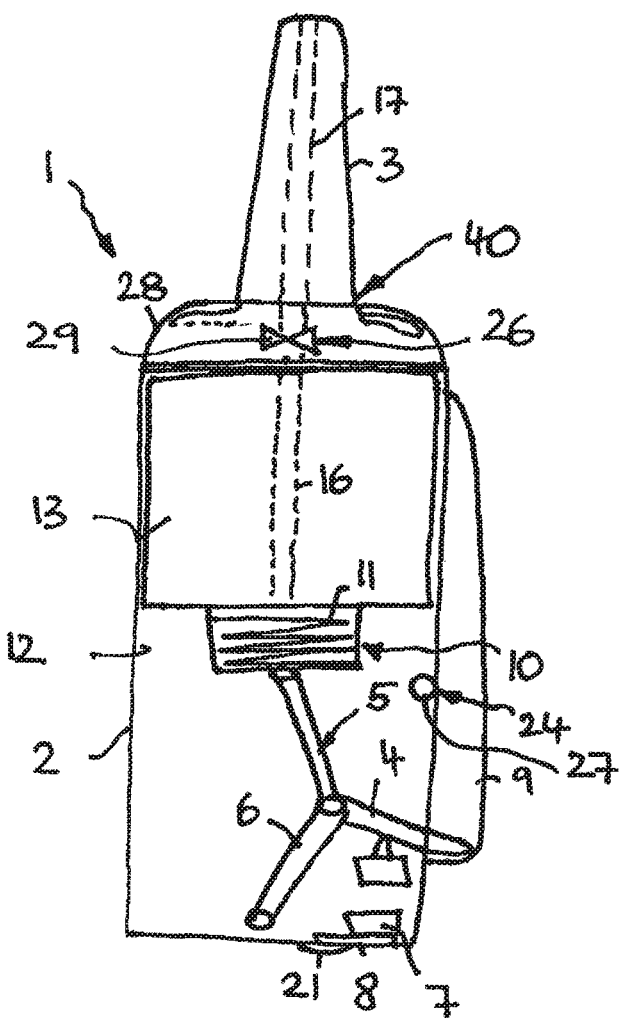
FIG. 1 shows a schematic representation of a nasal applicator in accordance with an advantageous embodiment of the invention in a starting position.

As FIG. 1 shows, the nasal applicator 1 can comprise an elongate, approximately cylindrical applicator housing 2 from which a dispensing pin 3 projects at the front face for introduction into a nasal cavity. The housing 2 can form a hand part for gripping the nasal applicator 1 and/or can form a receiving chamber 12 in its interior and can replaceably receive an active ingredient container 13 therein that is connectable to the dispensing pin 3 of the nasal applicator 1. To be able to change the active ingredient container 13, the housing 2 can, for example, be opened by a cover 28, the active ingredient container 13 can be inserted and the cover 28 can then be closed again.

The active ingredient container 13 together with the dispensing pin 3 can advantageously form a nasal spray cartridge or active ingredient cartridge known per se in which the active ingredient container 13 can be pressed onto the dispensing pin 3 to dispense the active ingredient by this stroke movement or compression movement. As FIG. 1 shows, the total active ingredient cartridge can be inserted into the applicator housing 2 when the cover 28 is removed. Said cover 28 is here pushed over the dispensing pin 3 and holds its fins tight when the cover 28 is closed again. The active ingredient container 13 is displaceably received in the applicator housing 2 so that the function of the active ingredient cartridge is maintained.

The discharge of the active ingredient from the inserted active ingredient container 13 advantageously takes place by a discharge actuator 26 that can, for example, be provided between the dispensing pin 3 and the active ingredient container 13 by means of which the active ingredient is propelled out of the active ingredient container 13. The active ingredient can here be conveyed via a cannula 16 that extends in the active ingredient container 13 via a pump 29 from where the active ingredient is further conveyed through a line 17 through the nasal pin 3 and is dispensed at the front face opening of the dispensing pin 3. As previously explained, said pump 29 can be integrated into the preconfigured active ingredient cartridge comprising the active ingredient container 13 and the dispensing pin 3.

To meter the active ingredient amount, said dispensing meter 40 in the form of the active ingredient cartridge in accordance with FIG. 1 can be actuated by an actuating button 9 at the housing 2.

Said actuating button 9 can, for example, be an actuation lever that is arranged at the peripheral side at the applicator housing 2 and that can be pressed into or moved toward the housing in the radial direction. Such an actuation adjustment movement of the actuating button 9 is transmitted to the dispensing meter via a transmitter 4, with in particular the active ingredient container 13 being able to be axially displaced in the longitudinal direction of the applicator housing 2 onto the dispensing pin 3 to hereby carry out a metering stroke. As FIG. 1 indicates, the movement of the transmitter 4 can be indirectly transmitted to the dispensing meter 40, in particular by means of a lever mechanism that implements the adjustment movement by a lever ratio. Such a lever mechanism 5 can comprise a toggle lever 6 that is supported at the applicator housing 2 and that can be stretched by a movement of the transmitter 4. This stretching movement of the toggle lever 6 can in turn be converted into a loading movement of a preload apparatus 10 that can, for example, have a spring device 11 in the form of a mechanical spring such as a spiral spring. Said preload apparatus 10 can then be triggered to actuate the dispensing meter in said manner.

Figure 3:
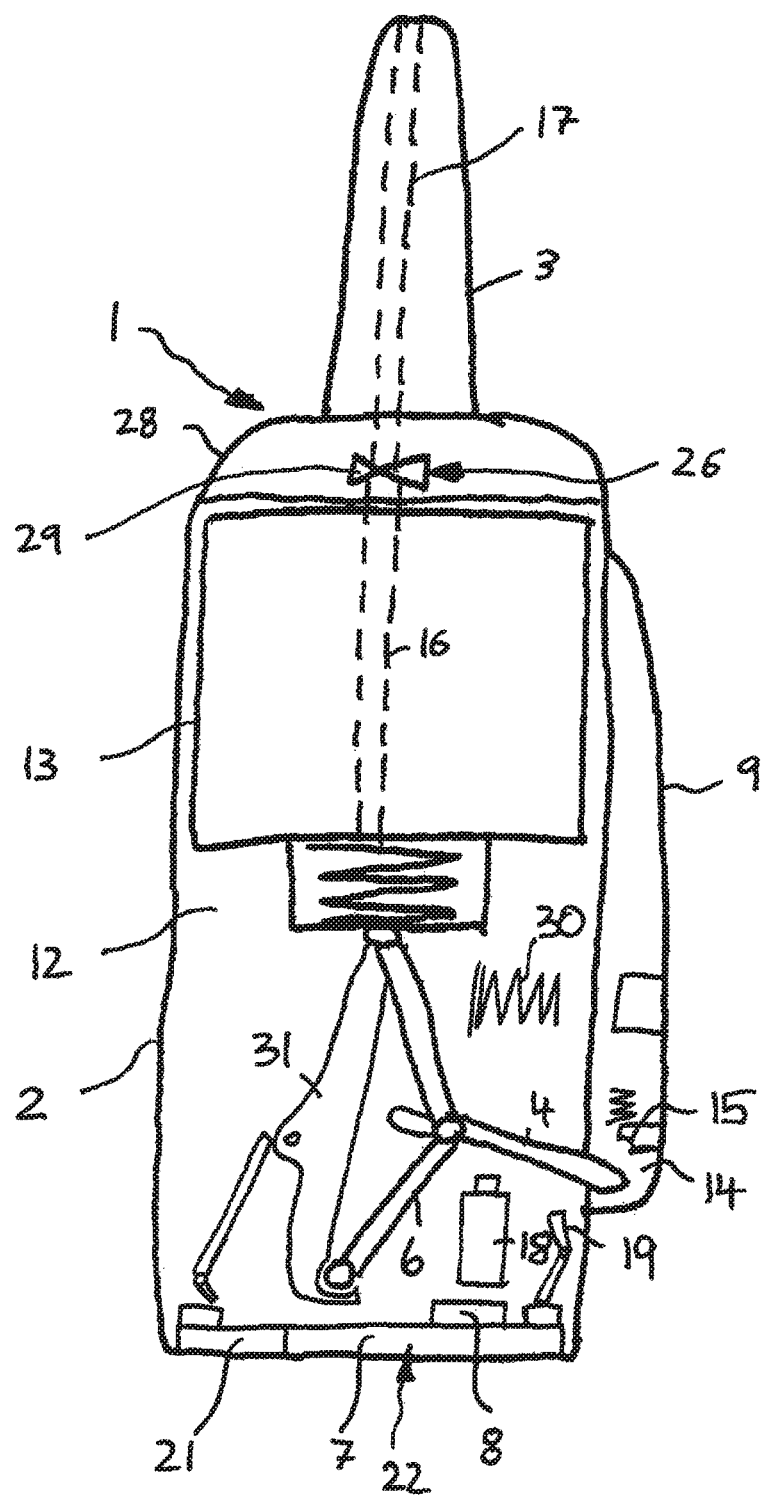
FIG. 3 shows a sectional, schematic representation of the actuation mechanism for actuating the active ingredient cartridge in a sectional view of the nasal applicator, with the transmitter to be actuated by the actuating button being shown in a decoupled starting position and with the preload apparatus being unloaded.

The design of the actuation mechanism and said actuation via the preload apparatus 10 will be explained in more detail in the following with reference to FIG. 3 to 7. As FIG. 3 shows, said transmitter 4 can be movably supported transversely to the longitudinal axis of the applicator housing 2 to be able to be moved by said actuating button 9. Said transmitter 4, that can, for example, form a rod-shaped, elongate element, can in particular be connected in an articulated manner to said toggle lever 6, for example in the region of its hinged joint.

Another end section of the transmitter 4 can extend in the region of the actuating button 9, with the actuating button 9 being able to have a cut-out 14 into which the transmitter 4 can travel to give the actuation button 9 a free-wheel or a free travel with respect to the transmitter 4.

Figure 5:
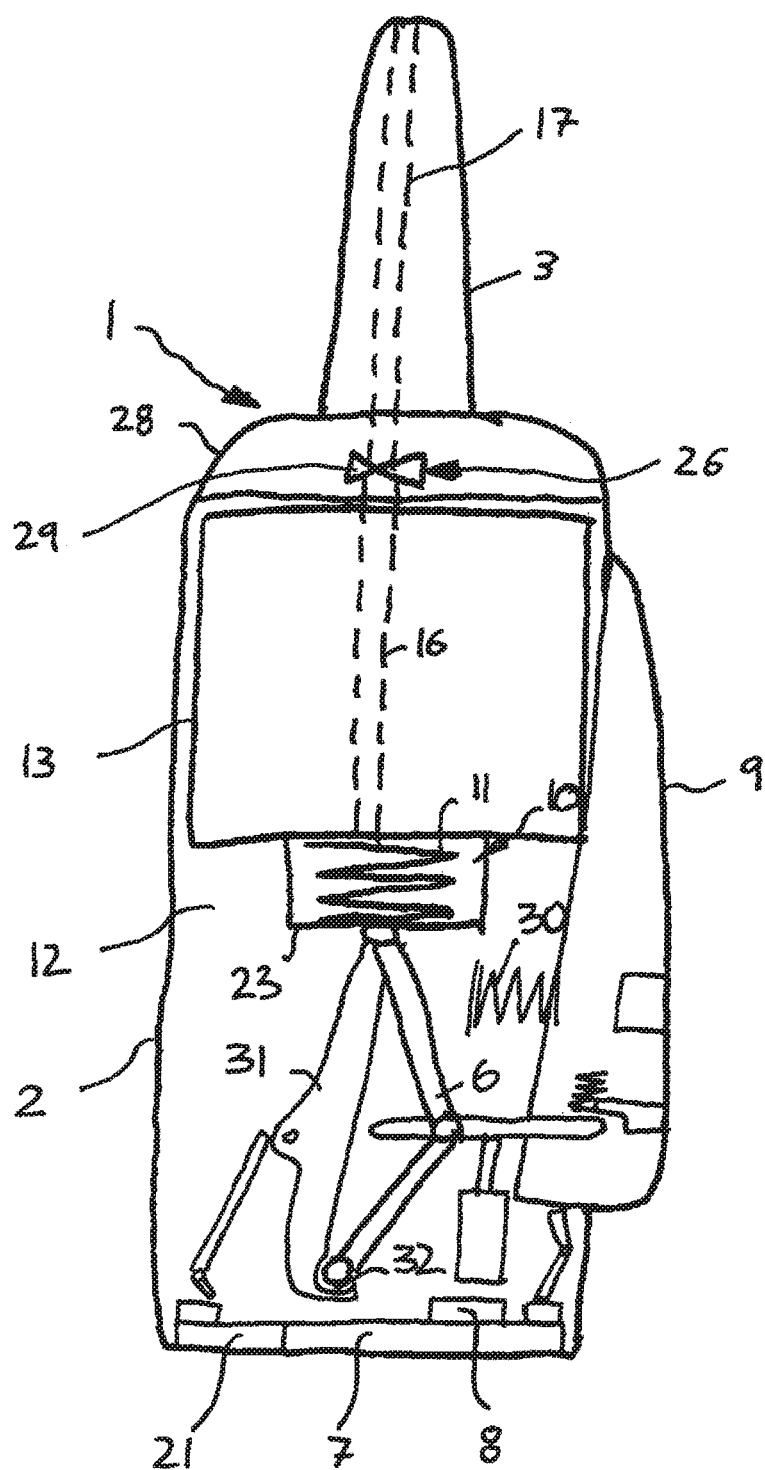
FIG. 5 shows a schematic sectional view of the actuation mechanism similar to FIGS. 3 and 4, with the actuating button being prior to a second actuation stroke and the transmitter having been traveled into its coupling position so that, on a further depression of the actuating button, the spring mechanism of the preload apparatus is loadable.

On the other hand, the actuation button 9 can have an engagement contour 15 in proximity to said cut-out 14 at which engagement contour the transmitter 4 can be supported to take up and implement an adjustment movement of the actuation button 9. As in particular FIG. 5 shows, said engagement contour 15 can form an abutment and/or can have a support surface at which the transmitter 4 can be supported in the direction of its desired direction of movement. Said engagement contour 15 can in particular extend approximately transversely to the predetermined direction of movement of the actuation button 9.

Said engagement contour 15 can advantageously form a shoulder whose one limb serves the guidance of the transmitter 4 and whose other limb serves the support in the desired direction of movement.

Figure 6:
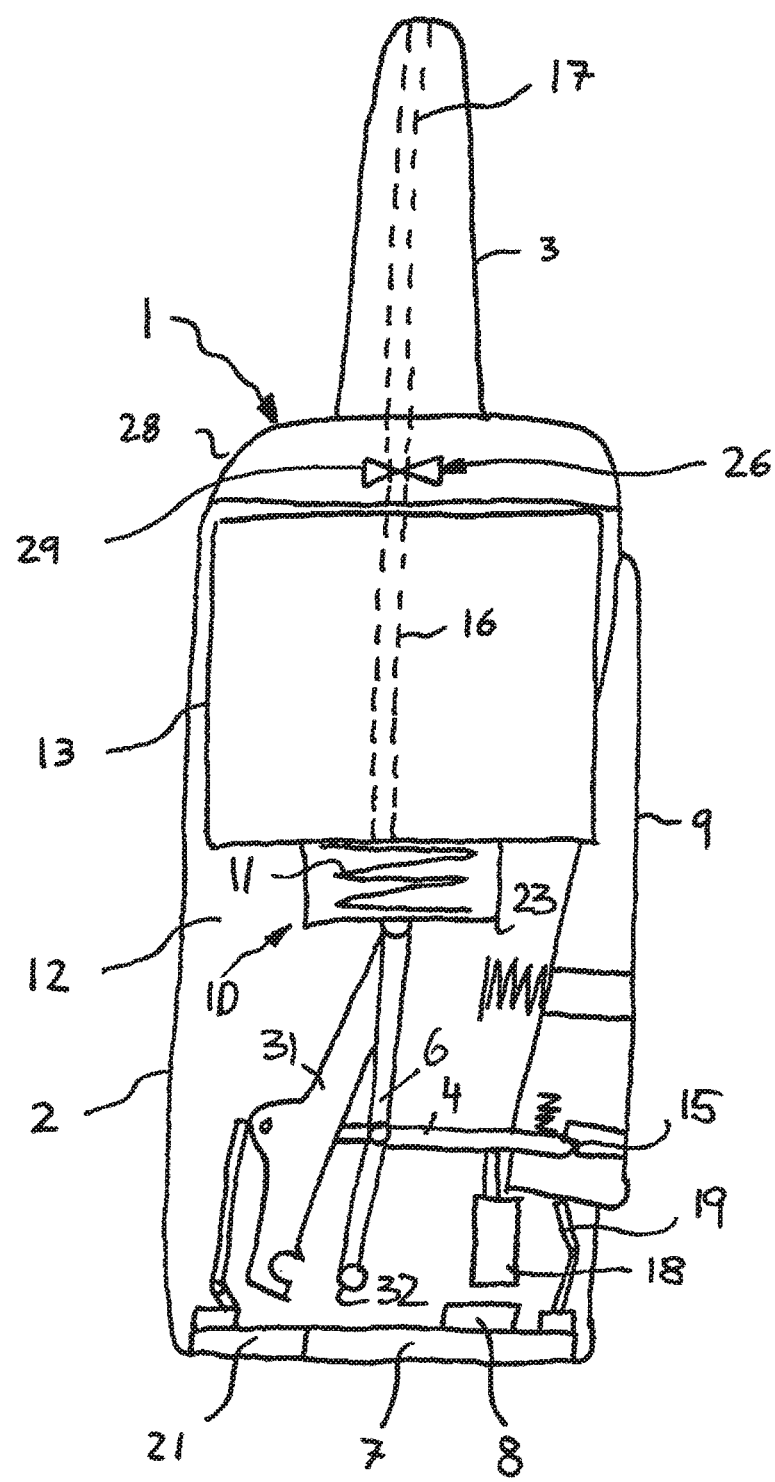
FIG. 6 shows a schematic sectional view of the actuation mechanism similar to FIGS. 3 to 5, with the transmitter still being in its coupling position and with the toggling lever mechanism having loaded the preload apparatus by a further depression of the actuating button, with the transmitter just triggering the retainer of the preload apparatus.

To be able to move the transmitter 4 to and fro between its decoupled starting position shown in FIG. 3 in which the transmitter 4 can move in free travel into the receiving pocket 14 of the actuation button 9 and the coupled active position or transmitter position such as FIGS. 5 and 6 show and in which the transmitter 4 is in engagement with the actuation button 9, an adjustment actuator 18 can be provided, for example in the form of an electromagnet or of another suitable actuator that is actuable by external energy and that can be controlled by a control apparatus 7.

The transmitter 4 can in particular be brought from its decoupled position into its coupled position in that the actuation button 9 is depressed or actuated once. Such an initially free-travel movement of the actuation button 9 is detected by a motion sensor 19 that can likewise be arranged in the applicator housing 2. Such a motion sensor 19 can be of different designs; it can, for example, work contactlessly. In this respect, different work principles are possible such as a light barrier and the like. A motion sensor 19 that works in a tactile manner can, however, advantageously also be provided that moves into contact with the actuation button 9 when the actuation button 9 is depressed.

If the motion sensor 19 indicates a movement of the actuation button 9, said adjustment actuator 18 can move the transmitter 4 into the coupled position as is shown by FIG. 5. However, before the adjustment actuator 18 is actually actuated, further operating parameters can be queried before the system in total is actually activated. The adjustment signal of the motion sensor 19 can in particular initially only be used to query dosage data and patient data such as an identification code, personal permitted dose and the like via the previously named electronic control apparatus 7.

This electronic control apparatus 7 can advantageously likewise be accommodated in the interior of the housing 2 and comprises a patient data store 8 from which the electronic control apparatus 7 can read out individually predefinable control data such as a maximum dosage, single dose or daily dose for a respective patient. Said control apparatus 7 and said patient data store 8 can, for example, be formed by a microcontroller and by associated circuit modules such as a storage element, with the patient data store 8 being able to be attached, for example, to the replaceable active ingredient container 13 or to the applicator housing 2 or being able to be connected to a store module attached thereto.

The control apparatus 7 can block the coupling of the transmitter 4 or can take it out of operation, for example when a maximum dose has been reached or when a release code is not present. To detect the actual dispensed amount, the nasal applicator 1 comprises a dose detection device that can, for example, be integrated into the control apparatus 7 and that counts the actuations of the dispensing pin and/or determines the length of the actuations.

Figure 2:
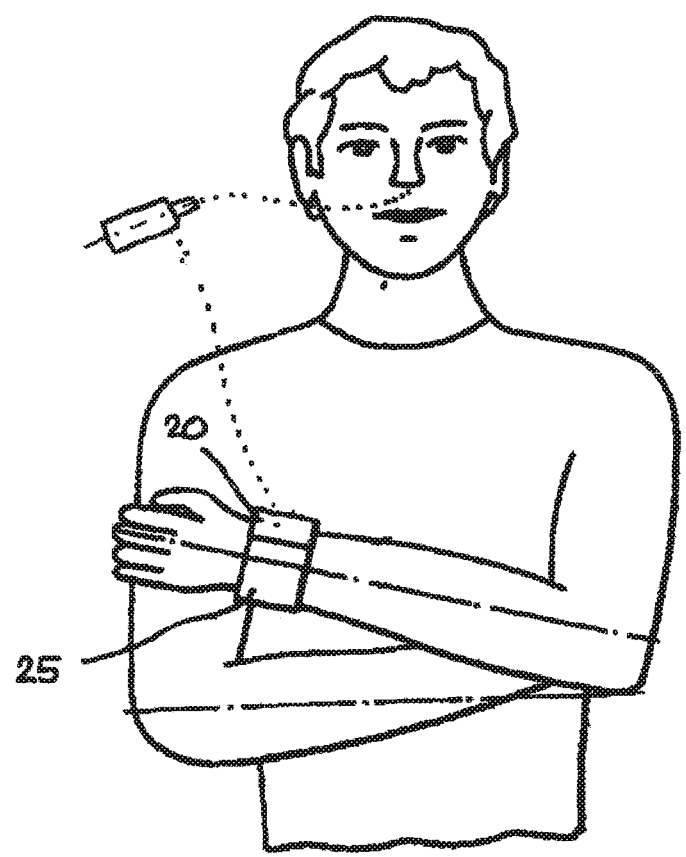
FIG. 2 shows a schematic representation of the nasal application that shows the interaction with an RFID arm band.

Alternatively or additionally, as FIG. 2 illustrates, the nasal applicator 1 or its control apparatus 7 can also communicate with an RFID element 20 that the patient wears on his body, for example by means of an arm band or of a different body fastening means 25. Control data individual to the patient, for example relating to the permitted maximum dose, can on the one hand, be stored in said RFID element 20 and/or a release code that releases the nasal applicator 1 at all or unlocks said blocking apparatus 6. The control apparatus 7 can, for this purpose, communicate with said RFID element 20 by means of an RFID transmission/reception device 21 if the nasal applicator is close enough to the patient.

Figure 4:
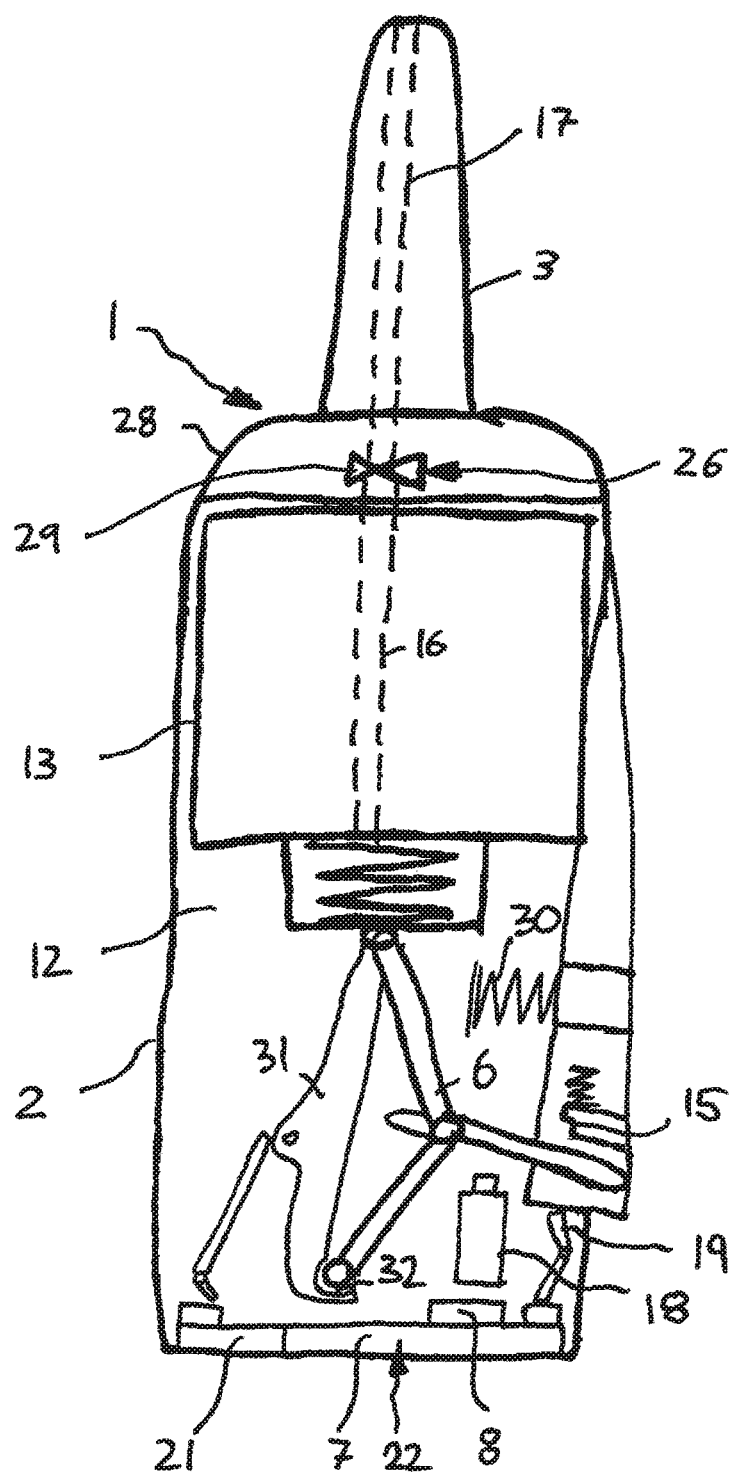
FIG. 4 shows a schematic sectional view of the actuation mechanism similar to FIG. 3, with the actuating button being depressed in the free travel in an activation or wake-up mode and having actuated a motion sensor.

If the data query of the control apparatus 7 shows that the nasal applicator can be released, the coupling switch 22 can instigate the coupling of the transmitter 4. As FIG. 4 shows, this is initially not yet possible if the actuation button 9 is not yet completely depressed or is still in the first free-travel actuation stroke. If, however, as FIG. 5 shows, the actuating button is released after the initialization of the system so that it can travel back into its starting position, which can be assisted by a spring device 30, said coupling switch 22 can move the transmitter 4 into its coupling position. More precisely, the adjustment actuator 18 in the form of the electromagnet can pivot the transmitter 4 in its engagement position in which the transmitter 4 contacts the step-shaped engagement contour 15 of the actuation button 9, cf. FIG. 5. If the actuation button 9 is then actuated or depressed, the front-face end of the transmitter 4 moves toward the flank of the engagement contour 15 extending transversely to the direction of actuation so that the transmitter 4 is held—by the actuation force on the actuation button 9—with friction engagement and/or with shape matching in the coupling position. The adjustment actuator 18 can here already be moved back again in a time-switched or also path-controlled manner—for example by a signal of the motion sensor 19—although FIG. 6 does not show this.

If the actuation button 9 is further depressed with a coupled position of the transmitter 4, the transmitter 4 moves in accordance with the adjustment movement of the actuating button 9 transversely to the longitudinal direction of the applicator housing 2. The toggle lever 6 is accordingly stretched, cf. for comparison FIGS. 5 and 6.

This stretching movement of the toggle lever 6 loads the spring device 11 of the preload apparatus 10 that is still held back by the retainer 31 via the loader 23 so that the cartridge is not yet actuated. Said retainer 31 can here be arranged in the further travel path of the transmitter 4 so that on a complete depression or actuation of the actuation button 9 in an end section of the movement of the transmitter 4, said transmitter 4 triggers the retainer 31, cf. for comparison FIGS. 5, 6 and 7. The retainer 31 can in particular—in rough terms—extend transversely to the direction of movement of the transmitter 4 and/or in the longitudinal direction of the applicator housing 2 so that the transmitter 4 presses against the retainer 31 in the end section of its adjustment movement and entrains it. The retainer 31 is hereby triggered. The shape matching to a retaining nose 32 at which the retainer 31 is otherwise held back in the active direction of the spring device 11 can release, for example. The retainer 31 can, for example, also be held in a spring-preloaded manner at said retaining nose 32 so that it can only trigger through the adjustment force of the transmitter 4.

Figure 7:
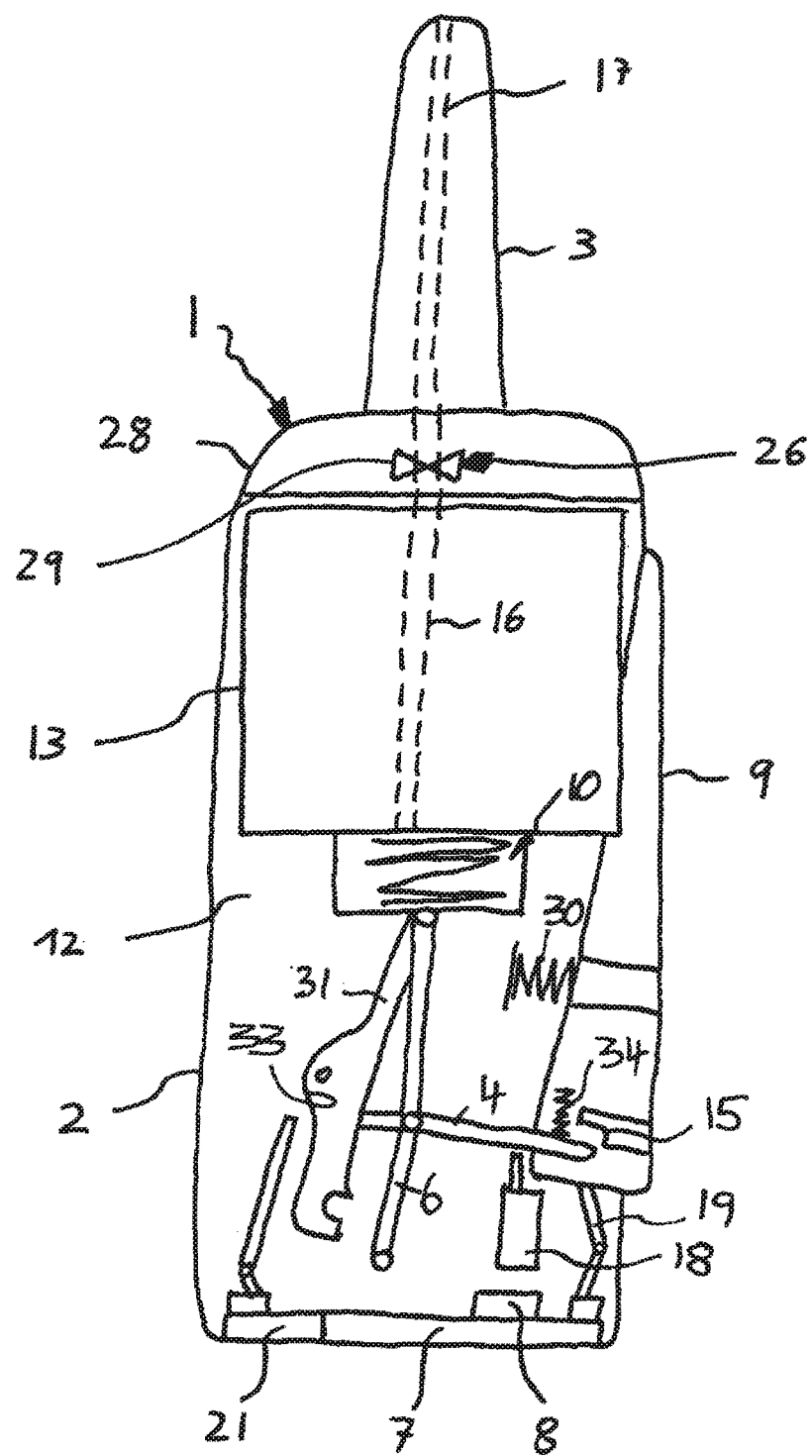
FIG. 7 shows a schematic sectional view of the actuation mechanism similar to FIGS. 3 to 6, with the retainer of the preload apparatus having been triggered and the transmitter having again been brought into a decoupled position.

If the retainer 31 triggers, as FIG. 7 shows, the spring device 11 of the preload apparatus 10 can spring out due to its loading force and can hereby actuate the dispensing meter; more precisely, it can move the active ingredient container 13 of the cartridge toward the dispensing pin 3, whereby a metering stroke is carried out.

The triggering retainer 31 can advantageously simultaneously move the transmitter 4 back into its decoupled position on the adjustment movement of the sprint 11 if it has not already itself returned into this decoupled position. The retainer 31 can, for example, have a returning nose 33 that acts on the transmitter 4 transversely to its adjustment movement or comes into engagement with the transmitter 4 on a movement of the retainer 31 in the direction of the spring force of the spring device 11, whereby the transmitter 4 is moved back into its decoupled position.

Such a return movement of the transmitter 4 can also be assisted and/or triggered and/or effected by a separate return spring 34, cf. FIG. 7.

On a release of the actuating button 9, the system as a whole moves back into its starting position again as is shown in FIG. 3.

To further protect the applicator from an imprudent actuation by small children, for example, alternatively or additionally to the aforesaid RFID release device, a mechanical actuation block 24 can optionally also be provided that blocks the actuation button 9 in its starting position and has to be released first to enable a depression of the actuation button 9. Such an actuation block 24 or child security lock can, for example, comprise one or more transverse latches 27 at the applicator housing 2 that are adjustable transversely to the plane of movement of the actuation button 9, for example by depressible unblocking buttons or unblocking jaws that can project laterally out of the applicator housing 2, cf. FIG. 1.

The described nasal applicator can in particular be used to administer high-strength opioid analgesics, with the nasal applicator generally also being able to be used, for example, for dispensing other medication that are administered under the control of the patient himself/herself. They can in particular be substances that are sensibly administered under at least one of the following conditions: a) The disease or complaints/symptoms to be treated have a sudden onset and cannot be predicted with sufficient accuracy (for example migraine attacks, nausea/vomiting, blood sugar fluctuations, epileptic fits, extreme blood pressure fluctuations); b) The medication used for treating the above-named symptoms are absorbed fast over the nasal mucous membrane and effect a fast improvement of the complaints; c) The medication used for treating the symptoms named under a) have a certain risk potential or have strong side effects, i.e. their application must be regulated within certain limits (for example, the so-called "triptans" can act fast and reliably on migraine attacks, but result in serious circulatory disorders on an overdose); d) The medication used for treating the symptoms named under a) can lead to dependence/addiction (examples: opioids, anticonvulsants) so that an access control or a patient identification has to take place as part of a patient-controlled application.

The invention claimed is:

1. A nasal applicator for nasal administration of medicinal active ingredients, comprising:
   an active ingredient store arranged in an applicator housing;
   a dispensing pin which is configured to be introduced into a nostril; and
   a dispensing meter for a metered dispensing of the active ingredient from an active ingredient container via the dispensing pin,
   wherein an actuating button movable by hand is movably supported at the applicator housing to be movable relative to the housing and relative to the ingredient container to actuate the dispensing meter whose actuation adjustment path is transmitted to the dispensing meter by a transmitter,
   wherein the dispensing meter has a loadable and releasable preload mechanism for actuating a metering conveyor with a defined preload force, and
   wherein the preload mechanism is designed as loadable by the transmitter against a retainer which is releasable by the transmitter so that the preload mechanism is loadable as well as releasable by the transmitter.

2. The nasal applicator in accordance with claim 1, wherein the medicinal active ingredients are analgesics.

3. The nasal applicator in accordance with claim 1, wherein the preload mechanism has a toggle lever that is stretchable by the transmitter and loads a spring device against the retainer.

4. The nasal applicator in accordance with claim 3, wherein the transmitter is coupled to the toggle lever in an articulated manner.

* * * * *